United States Patent
Pahk et al.

(10) Patent No.: US 12,053,198 B2
(45) Date of Patent: Aug. 6, 2024

(54) APPARATUS AND METHOD FOR PRECISE MECHANICAL TISSUE ABLATION USING PRESSURE MODULATED FOCUSED ULTRASOUND

(71) Applicant: KOREA INSTITUTE OF SCIENCE AND TECHNOLOGY, Seoul (KR)

(72) Inventors: Ki Joo Pahk, Seoul (KR); Hyung Min Kim, Seoul (KR); Byung Chul Lee, Seoul (KR); Inchan Youn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 443 days.

(21) Appl. No.: 16/857,956

(22) Filed: Apr. 24, 2020

(65) Prior Publication Data
US 2021/0169515 A1 Jun. 10, 2021

(30) Foreign Application Priority Data
Dec. 6, 2019 (KR) ........................ 10-2019-0161955

(51) Int. Cl.
*A61B 17/32* (2006.01)
*A61B 17/00* (2006.01)
(Continued)

(52) U.S. Cl.
CPC ........ *A61B 17/320068* (2013.01); *A61N 7/02* (2013.01); *A61B 2017/00084* (2013.01);
(Continued)

(58) Field of Classification Search
CPC .............. A61N 7/02; A61N 2007/0039; A61N 2007/0078; A61B 2018/00577;
(Continued)

(56) References Cited

U.S. PATENT DOCUMENTS 5,601,526 A * 2/1997 Chapelon ................. A61N 7/02
601/3
5,643,179 A * 7/1997 Fujimoto ................. A61N 7/02
601/3
(Continued)

FOREIGN PATENT DOCUMENTS

JP 5998017 B2 9/2016
JP 6161447 B2 7/2017
(Continued)

OTHER PUBLICATIONS

E. Vlaisavljevich et al., "Histotripsy-Induced Cavitation Cloud Initiation Thresholds in Tissues of Different Mechanical Properties", IEEE Transactions on Ultrasonics, Ferroelectrics, and Frequency Control, vol. 61, No. 2, pp. 341-352, Feb. 2014 (Year: 2014).*
(Continued)

*Primary Examiner* — Joel Lamprecht
*Assistant Examiner* — Nyrobi Celestine
(74) *Attorney, Agent, or Firm* — Birch, Stewart, Kolasch & Birch, LLP

(57) ABSTRACT

An apparatus for tissue ablation according to an embodiment of the present disclosure includes an ultrasound output unit to output focused ultrasound, and a control unit to control an intensity of the focused ultrasound, wherein the control unit may be configured to control the intensity of the focused ultrasound below a setting value, when a first condition in which a vapor bubble is formed in a tissue or a second condition in which a temperature of the tissue reaches a threshold is accomplished during the output of the focused ultrasound to the tissue. According to this embodiment, it is possible to precisely control vapor bubble dynamics without generating the shockwave scattering effect by instantaneously controlling the acoustic pressure and the intensity of
(Continued)

the focused ultrasound, and prevent damage to a tissue other than a lesion to be removed.

16 Claims, 22 Drawing Sheets

(51) Int. Cl.
*A61B 90/00* (2016.01)
*A61N 7/00* (2006.01)
*A61N 7/02* (2006.01)

(52) U.S. Cl.
CPC .............. *A61B 2017/00132* (2013.01); *A61B 2017/0019* (2013.01); *A61B 2017/320069* (2017.08); *A61B 2090/0472* (2016.02); *A61N 2007/0039* (2013.01)

(58) Field of Classification Search
CPC .. A61B 2090/0472; A61B 2018/00642; A61B 2018/00791
See application file for complete search history.

(56) References Cited

U.S. PATENT DOCUMENTS

| | | | |
|---|---|---|---|
| 9,504,451 B2* | 11/2016 | Tamano | A61B 8/5223 |
| 9,683,970 B2 | 6/2017 | Tateyama | |
| 2006/0058671 A1* | 3/2006 | Vitek | A61N 7/02 |
| | | | 600/447 |
| 2007/0161902 A1* | 7/2007 | Dan | A61B 17/22004 |
| | | | 600/458 |
| 2009/0270730 A1* | 10/2009 | Azuma | A61B 8/485 |
| | | | 600/443 |
| 2009/0287205 A1* | 11/2009 | Ingle | A61B 18/14 |
| | | | 606/34 |
| 2010/0069797 A1* | 3/2010 | Cain | A61B 17/22004 |
| | | | 601/2 |
| 2010/0100014 A1* | 4/2010 | Eshel | A61N 7/00 |
| | | | 601/2 |
| 2010/0241036 A1* | 9/2010 | Vortman | A61N 7/02 |
| | | | 601/3 |
| 2012/0271169 A1* | 10/2012 | Coussios | A61N 7/02 |
| | | | 600/439 |
| 2013/0018285 A1* | 1/2013 | Park | A61N 7/02 |
| | | | 601/2 |
| 2014/0005521 A1* | 1/2014 | Kohler | A61B 6/4057 |
| | | | 601/3 |
| 2015/0119763 A1 | 4/2015 | Canney et al. | |
| 2015/0258352 A1* | 9/2015 | Lin | A61B 17/22004 |
| | | | 601/2 |
| 2015/0351822 A1* | 12/2015 | Mulcahey | A61B 90/98 |
| | | | 606/22 |
| 2016/0184616 A1* | 6/2016 | Cain | A61N 7/00 |
| | | | 601/2 |
| 2017/0072227 A1 | 3/2017 | Khokhlova et al. | |
| 2017/0100145 A1* | 4/2017 | Khoklova | A61N 7/02 |
| 2017/0105783 A1* | 4/2017 | Highsmith | A61B 18/1492 |
| 2017/0281984 A1* | 10/2017 | Marquet | G01R 33/4804 |
| 2019/0201089 A1* | 7/2019 | Waldstreicher | A61B 18/1492 |
| 2021/0128229 A1* | 5/2021 | Panescu | A61B 18/1492 |

FOREIGN PATENT DOCUMENTS

| | | |
|---|---|---|
| JP | 6271846 B2 | 1/2018 |
| KR | 10-2012-0081384 A | 7/2012 |
| KR | 10-2015-0112359 A | 10/2015 |
| WO | WO-2017077605 A1 * | 5/2017 |

OTHER PUBLICATIONS

H. M. Strunk et al., "Clinical Use of High-Intensity Focused Ultrasound (HIFU) for Tumor and Pain Reduction in Advanced Pancreatic Cancer," Fortschr Röntgenstr, vol. 188, pp. 662-670, Jan. 2016 (Year: 2016).*
K. B. Bader et al., "The influence of gas diffusion on bubble persistence in shock-scattering histotripsy", The Journal of Acoustical Society of America, vol. 143, No. 6, pp. EL481-EL486, Jun. 2018 (Year: 2018).*
T. Khokhlova et al, "Controlled tissue emulsification produced by high intensity focused ultrasound shock waves and millisecond boiling", The Journal of the Acoustical Society of America, vol. 130, No. 5, pp. 3498-3510, Nov. 2011 (Year: 2011).*
A. Maxwell et al, "Disintegration of Tissue Using High Intensity Focused Ultrasound: Two Approaches That Utilize Shock Waves", Acoustics Today, vol. 8, No. 4, pp. 24-36, Oct. 2012 (Year: 2012).*
A. Eranki et al, "Boiling histotripsy lesion characterization on a clinical magnetic resonance imaging-guided high intensity focused ultrasound system", PLoS One, vol. 12, No. 3, pp. 1-23, Mar. 2017 (Year: 2017).*
T. Khokhlova et al, "Dependence of Boiling Histotripsy Treatment Efficiency on HIFU Frequency and Focal Pressure Levels", Ultrasound in Medicine and Biology, vol. 43, No. 9, pp. 1975-1985, Apr. 2017 (Year: 2017).*
WO-2017077605-A1 (Year: 2017).*
Pahk et al., "Mechanical damage induced by the appearance of rectified bubble growth in a viscoelastic medium during boiling histotripsy exposure", Ultrasonics—Sonochemistry, 2019, vol. 53, pp. 164-177.
Pahk et al., "Numerical and Experimental Study of Mechanisms Involved in Boiling Histotripsy", Ultrasound in Medicine and Biology, 2017, vol. 43, Issue 12, pp. 2848-2861.

* cited by examiner

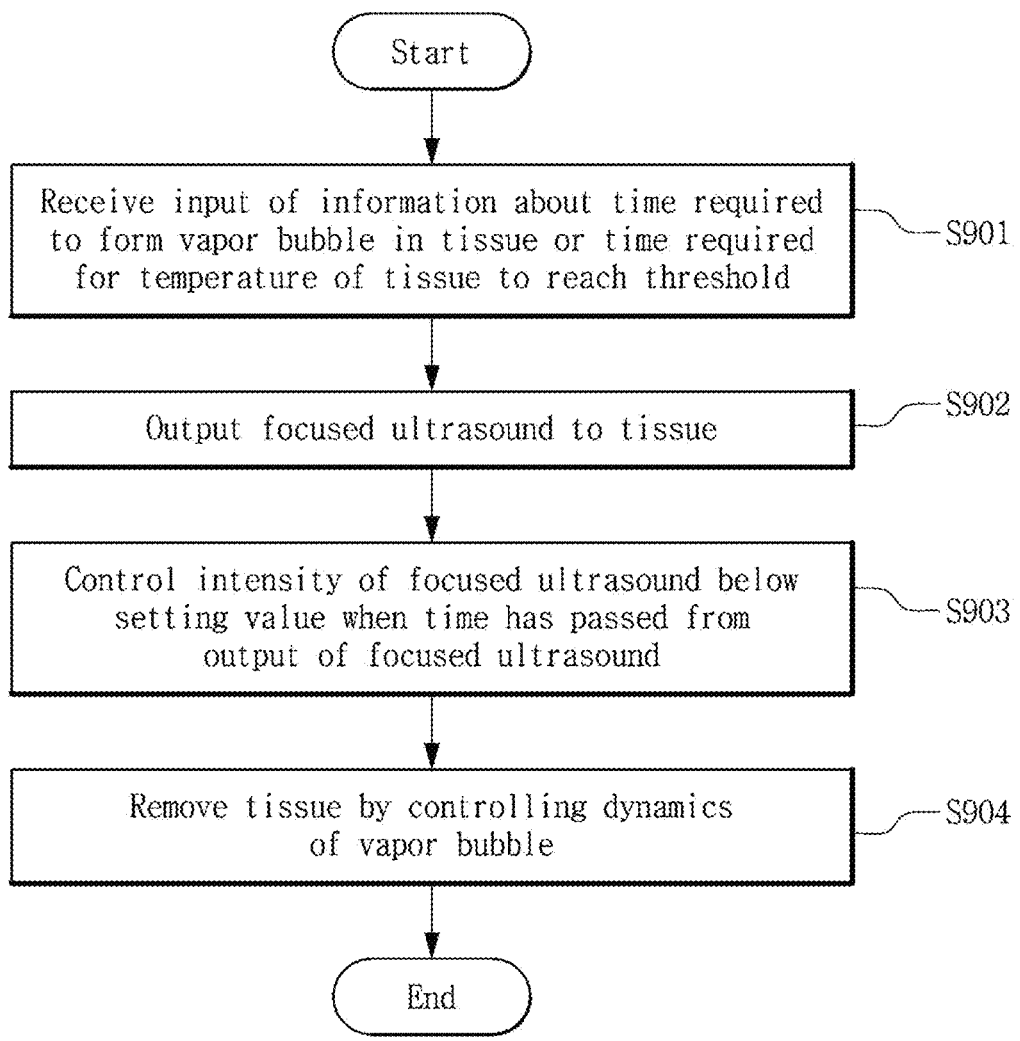

APPARATUS AND METHOD FOR PRECISE MECHANICAL TISSUE ABLATION USING PRESSURE MODULATED FOCUSED ULTRASOUND

DESCRIPTION OF GOVERNMENT-FUNDED RESEARCH AND DEVELOPMENT

This research is conducted by Korean Institute of Science and Technology and funded by the Creative Convergence Research Program (development of personalized neuroplasticity assessment and enhancement based stroke-related impairment recovery technology, project serial number: CAP-18-01-KIST) in the Ministry of Science and ICT.

CROSS-REFERENCE TO RELATED APPLICATION

This application claims priority to Korean Patent Application No. 10-2019-0161955, filed on Dec. 6, 2019, and all the benefits accruing therefrom under 35 U.S.C. § 119, the contents of which in its entirety are herein incorporated by reference.

BACKGROUND

1. Field

The present disclosure relates to an apparatus and method for tissue ablation using intensity modulated and pressure modulated focused ultrasound, and more particularly, to technology for more precise tissue ablation by controlling vapor bubble dynamics without the shock scattering effect by instantaneously reducing the acoustic pressure and intensity of high intensity focused ultrasound.

2. Description of the Related Art

To conduct therapy that mitigates a patient's pain or stimulates neural cell in a specific human body part, a method that inserts electrodes into the patient's human body has been used, but there is a risk that the human body may be damaged by this mechanical invasion process.

Recently, ultrasound stimulation therapy that can stimulate an affected part without a mechanical invasion process is widely used. Ultrasound may be classified into high intensity focused ultrasound (HIFU) and low intensity focused ultrasound (LIFU) according to the intensity, and it is known that high intensity focused ultrasound is used for direct treatment, for example, ablation of human body tissues such as cancer cells, tumors and lesions, while low intensity focused ultrasound can obtain medical effects without damaging human body tissues.

The unit of ultrasound intensity is indicated by spatial-peak temporal-average intensity (Ispta) and spatial-peak pulse average intensity (Isppa) according to the Acoustic Output Measurement Standard for Diagnostic Ultrasound Equipment by American Institute for Ultrasound in Medicine and National Electronics Manufacturers Administration (NEMA).

In particular, high intensity ultrasound has the Ispta of 3 W/cm$^2$ or above, and the use of high intensity focused ultrasound makes it possible to transmit strong acoustic energy that is a few ten to a few hundred times greater than the atmospheric pressure to a desired part in the body in a completely non-invasive manner, and the transmitted acoustic energy is converted to thermal or mechanical energy, thereby directly removing the tissue.

Thermal energy based high intensity focused ultrasound induces thermal coagulative necrosis of tissue by focusing ultrasonic energy of a predetermined acoustic intensity or above onto a point to generate high temperature heat at the focal point. This method is being widely used in clinical applications for the purpose of treatment of diseases such as uterine fibroids, adenomyosis, myoma uteri, benign prostatic hyperplasia, prostate cancer, metastatic brain tumor and essential tremor.

Recently, in addition to the thermal ablation effect using thermal energy, mechanical ablation of soft tissues using focused ultrasound is being studied. This is called 'mechanical tissue fractionation' or 'boiling histotripsy', and mechanically fractionates the surrounding tissues by artificially creating acoustic cavitation at the focal point of ultrasound using the pressure that is a few ten times higher than acoustic pressure used in the existing high intensity focused ultrasound. The boiling histotripsy requires a shorter treatment time than the existing high intensity ultrasound treatment, and can monitor the treatment process through mechanical tissue ablation and real-time cavitation monitoring, and thus is gaining attention as next-generation promising ultrasonic surgery technology in clinical applications.

FIG. 1A to 1E show each step of a tissue ablation process through focused ultrasound soft tissue ablation according to the related art. Referring to FIG. 1A to 1E, when high intensity ultrasound is outputted to a target tissue (a lesion such as a tumor) using an ultrasonic transducer, a shockwave is produced at the focal point part onto which ultrasound is focused (FIG. 1A), as the tissue is heated by shock wave heating, a primary boiling bubble is formed at the focal point (FIG. 1B), the vapor bubble grows (rectified bubble growth) due to the asymmetry in a shockwave and water vapor that transports into the bubble (FIG. 10). As described above, cavitation occurs in which a small cavity and a bubble are formed in a medium by ultrasound, and the bubble oscillates and collapses with changes in acoustic pressure, inducing a mechanical damage. Boiling histotripsy refers to tissue ablation through the mechanical stresses produced by the acoustic cavitation.

However, in a general boiling histotripsy irradiation condition, a shock scattering effect occurs due to the interaction between the boiling vapor bubble and the incoming incident shockwaves, and accordingly, numerous bubble clouds are generated in front of the primary vapor bubble towards the ultrasonic transducer (FIG. 1D). The shear forces produced around oscillating boiling vapor bubbles in a localized heated region within the HIFU focal volume can tear off tissue and inertial cavitation clouds that form in between the boiling bubble and the transducer enable the mechanical disruption of tissue through violent bubble collapses. Eventually, the tissue is removed in the shape of a tadpole, not a circle (FIG. 1E).

FIGS. 2A to 2C are diagrams illustrating the principle of a shock scattering effect and bubble cloud formation in boiling histotripsy according to the related art. Referring to FIGS. 2A to 2C, high intensity focused ultrasound outputted by the ultrasonic transducer produces a strong shockwave at the focal point position (FIG. 2A). Shock wave heating then occurs at the focus, resulting in the formation of a primary boiling bubble. An incoming incident shockwave is reflected and inverted by the primary vapor bubble due to the acoustic impedance mismatch, and this scattered shockwave overlaps the incoming incident rarefactional phase of a shockwave pulse, forming a stronger negative pressure field, and in this instance, bubble clouds are formed (FIG. 2B). The interaction of incoming shockwaves with the bubbles continuously produces the shock scattering effect, and as a consequence, numerous bubble clouds are produced between the ultrasonic transducer and the primary vapor bubble (FIG. 2C).

The bubble clouds generated by the shock scattering effect produce mechanical stresses at areas other than focal point position, causing potential damage to an unwanted tissue part. Accordingly, boiling histotripsy can be only used to remove tissues of a wide range, and cannot be applied to surgery requiring precision, for example, near important blood vessels.

SUMMARY

The present disclosure is designed to solve the above-described problems, and therefore the present disclosure is directed to providing tissue ablation that can be applied to lesions of various sizes by precisely controlling vapor bubble dynamics without producing the shock scattering effect through pressure/intensity modulated or pulse modulated focused ultrasound.

An apparatus for tissue ablation using intensity modulated focused ultrasound according to an embodiment of the present disclosure includes an ultrasound output unit to output focused ultrasound, and a control unit to control a pressure and an intensity of the focused ultrasound, wherein the control unit may control to reduce the acoustic pressure and the intensity of the focused ultrasound, when a first condition in which a vapor bubble is formed in a tissue or a second condition in which a temperature of the tissue reaches a threshold is accomplished during the output of the focused ultrasound to the tissue.

In an embodiment, the control unit may control the intensity of the focused ultrasound below a setting value when the first condition or the second condition is accomplished, and the focused ultrasound having the intensity below the setting value may not produce the shock scattering effect in the tissue.

In an embodiment, the setting value may be set according to a type of the tissue and characteristics of the focused ultrasound.

In an embodiment, the control unit may control the intensity and the pressure of the focused ultrasound by adjusting an acoustic pressure, a waveform, a frequency, or an irradiation time of the ultrasound outputted from the ultrasound output unit.

In an embodiment, the ultrasound output unit may be configured to output high intensity focused ultrasound having a shockwave pressure of 50 MPa or above or a peak positive acoustic pressure of 40 MPa or above and a peak negative pressure of −10 MPa or below at the focal point, and when the first condition or the second condition is accomplished, the control unit may control the shockwave pressure of the focused ultrasound below 50 MPa or to the peak positive pressure of 40 MPa or below and the peak negative pressure of −10 MPa or above.

In an embodiment, the apparatus may further include a first detection unit to detect if the first condition is accomplished, and the first detection unit may include a signal sensor to sense a change in acoustic signal or electrical signal caused by the vapor bubble formation and dynamics.

In an embodiment, the apparatus may further include a second detection unit to detect if the second condition is accomplished, and the second detection unit may include a temperature sensor to sense a change in temperature of the tissue.

In an embodiment, the control unit may be configured to control the intensity and the acoustic pressure of the focused ultrasound below the setting value, when time has passed from start of the output of the focused ultrasound to the tissue, based on information about the time required to accomplish the first condition or the second condition.

In an embodiment, the time required to accomplish the first condition or the second condition may be determined based on biomechanics information, thermodynamics information and bubble dynamics information.

In an embodiment, when the first condition or the second condition is accomplished, the control unit may control the ultrasound output unit not to output the focused ultrasound, so that part of the tissue may be removed only using a mechanical stress produced when the vapor bubble is formed.

A method for controlling focused ultrasound for precise tissue ablation according to an embodiment of the present disclosure includes outputting focused ultrasound to a tissue, determining if a first condition in which a vapor bubble is formed in the tissue or a second condition in which a temperature of the tissue reaches a threshold is accomplished, performing control to reduce an acoustic pressure and an intensity of the focused ultrasound when the first condition or the second condition is accomplished, and removing part of the tissue using dynamics of the vapor bubble formed in the tissue.

In an embodiment, performing control to reduce the acoustic pressure and the intensity of the focused ultrasound may include controlling the pressure and/or intensity of the focused ultrasound below a setting value, and the focused ultrasound having the pressure and/or intensity below the setting value may not produce the shock scattering effect in the tissue.

In an embodiment, in the output of the focused ultrasound to the tissue, the focused ultrasound may have a shockwave pressure of 50 MPa or above or a peak positive pressure of 40 MPa or above and a peak negative pressure of −10 MPa or below at the focal point, and the focused ultrasound after controlling the pressure and/or intensity of the focused ultrasound below the setting value may have the shockwave pressure of less than 50 MPa or the peak positive pressure of 40 MPa or below and the peak negative pressure of −10 MPa or above.

In an embodiment, determining if the first condition or the second condition is accomplished may include sensing a change in acoustic signal or electrical signal caused by the vapor bubble formation and dynamics; or sensing a change in temperature of the tissue.

In an embodiment, the method may further include receiving an input of information about time required to accomplish the first condition or the second condition, and controlling the intensity of the focused ultrasound below a setting value when the time has passed from start of the output of the focused ultrasound to the tissue, based on the information.

In an embodiment, controlling the acoustic pressure and the intensity of the focused ultrasound below the setting value may include stopping outputting the focused ultrasound when the first condition or the second condition is accomplished, and removing part of the tissue may be performed only using a mechanical stress produced when the vapor bubble is formed.

There may be provided a computer program stored in a computer-readable recording medium, for performing the method for controlling focused ultrasound for precise tissue ablation according to an embodiment.

According to an embodiment of the present disclosure, it is possible to precisely control vapor bubble dynamics without inducing the shock scattering effect by instantaneously controlling the pressure and/or intensity of focused ultrasound after when a vapor bubble is formed in the tissue or the temperature reaches the threshold during the output of focused ultrasound to the tissue. Accordingly, it is possible to prevent damage to areas other than a target lesion and improve the precision of tissue ablation. Therefore, it is possible to selectively remove only a specific cell through precise control of vapor bubble.

BRIEF DESCRIPTION OF THE DRAWINGS

FIG. 10 is a flowchart showing a method for tissue ablation using intensity modulated focused ultrasound according to another embodiment.

DETAILED DESCRIPTION

Figure 1A:
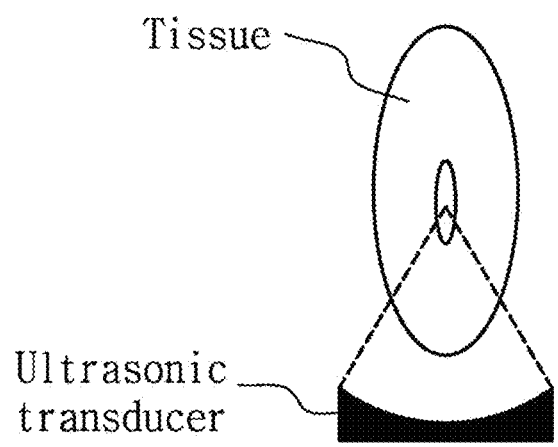
FIGS. 1A to 1E show a tissue ablation process using focused ultrasound according to the related art.
Figure 1B:
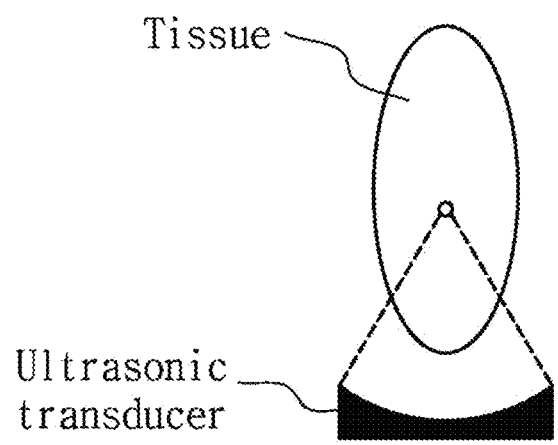
Figure 1C:
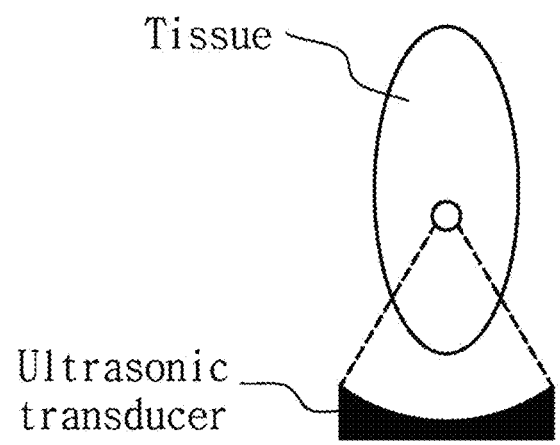
Figure 1D:
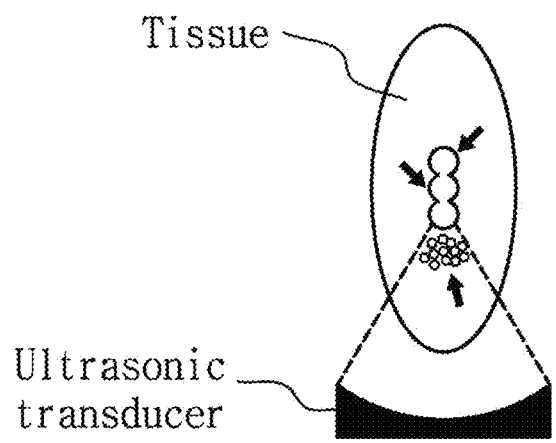
Figure 1E:
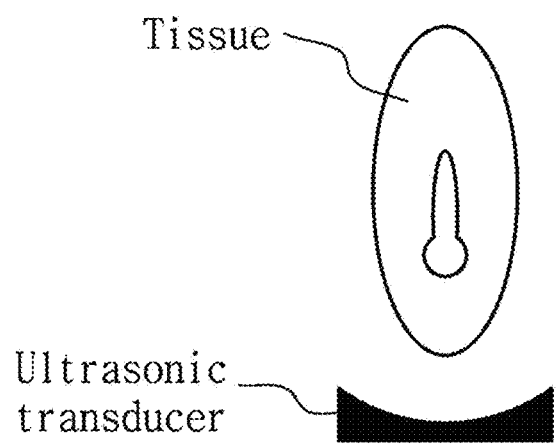

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

The terms as used herein are general terms selected as those being now used as widely as possible in consideration of functions, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, it should be noted that the terms as used herein should be interpreted based on the substantial meaning of the terms and the context throughout the specification, rather than simply the name of the terms.

Hereinafter, exemplary embodiments of an apparatus and method for tissue ablation using intensity modulated focused ultrasound will be described in detail with reference to the accompanying drawings.

Figure 3A:
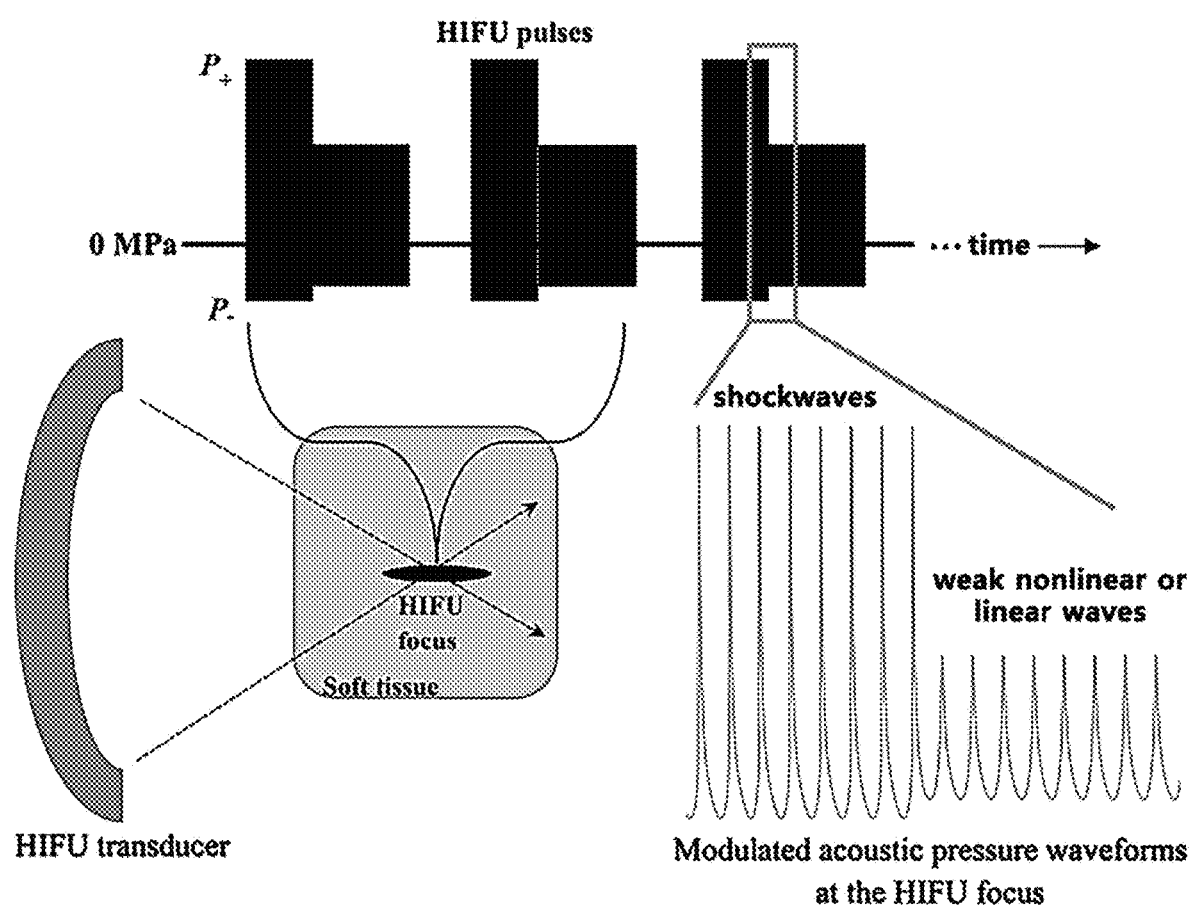
FIG. 3A shows a conceptual diagram illustrating a technique for removing a tissue using intensity modulated focused ultrasound according to an embodiment.

FIG. 3A shows a conceptual diagram illustrating a technique for removing a tissue using intensity modulated focused ultrasound according to an embodiment. When a high intensity focused ultrasound (HIFU) transducer outputs ultrasound, the ultrasound focuses on the focal point in the soft tissue. Shock waves with high acoustic pressures can be formed at the HIFU focus and then vapor bubbles are subsequently generated by the shock wave heating. Bubble clouds generated by the shock wave scattering effect produce mechanical stresses at areas other than the focal point position, causing potential damage to an unwanted tissue part.

According to an embodiment, it is possible to precisely control vapor bubble dynamics without inducing the shock scattering effect by controlling the pressure and/or intensity of focused ultrasound to minimize the shock wave scattering effect. As shown in FIG. 3A, the HIFU waveform repeats high intensity waves that generate shock waves and weak nonlinear or linear waves that minimize the shock wave scattering effect. Thereby, it is possible to prevent cavitation clouds, which are caused by the shock wave scattering effect, from damaging unwanted tissue area.

Figure 3B:
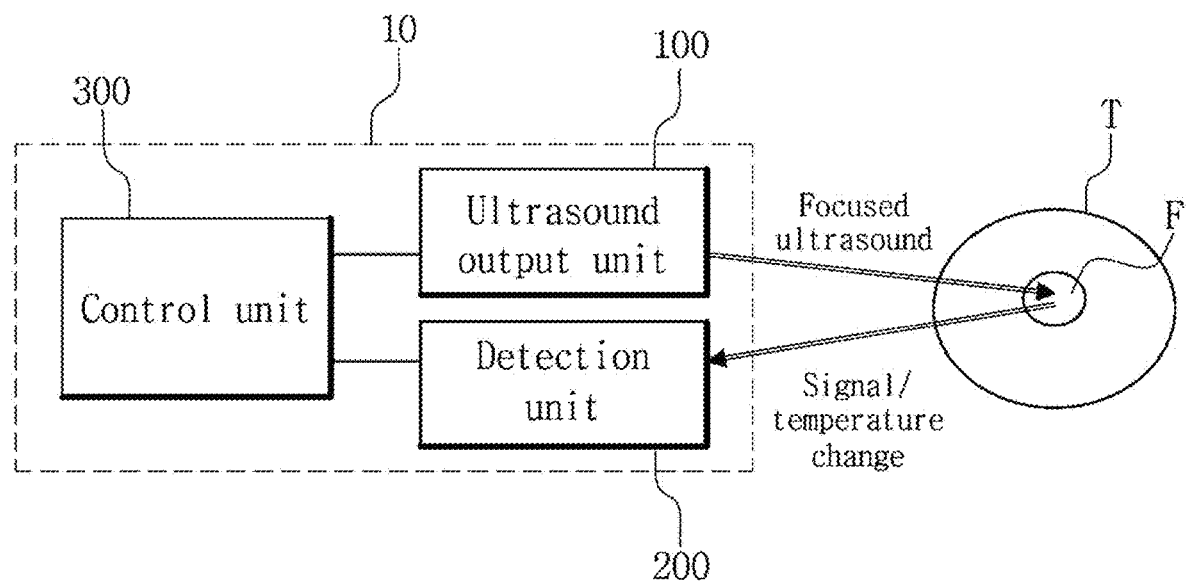
FIG. 3B shows a configuration of an apparatus for tissue ablation using intensity modulated focused ultrasound according to an embodiment.

FIG. 3B shows the configuration of the apparatus for tissue ablation using pressure or intensity modulated focused ultrasound according to an embodiment. Referring to FIG. 3B, the apparatus 10 for tissue ablation according to an embodiment may include an ultrasound output unit 100, a detection unit 200 and a control unit 300. For reference, FIG. 3B shows only necessary components for describing the present disclosure, and does not depict all essential components for operating the apparatus or obtaining the effect of the invention. That is, in addition to the above-described components, the apparatus 100 for tissue ablation may further include an additional hardware and/or software component for obtaining the effect of the invention.

The ultrasound output unit 100 includes an ultrasonic transducer to output focused ultrasound. The ultrasonic transducer is a sound source that outputs ultrasound, and may output high intensity ultrasound of 3 W/cm² of above (Ispta). According to an embodiment, the ultrasound output unit 100 may include a single transducer or an array of transducers to focus ultrasound onto one focal point. The ultrasound output unit 100 is connected to the control unit 300 as described below, and is configured to receive a control signal that determines the characteristics of ultrasound, for example, acoustic pressure, waveform, frequency, from the control unit 300, and output ultrasound of the intensity of a set value.

In general, an ultrasonic transducer converts alternating current energy of 20 KHz or above to mechanical vibration of the same frequency using the piezoelectric effect or magnetostrictive effect. For example, the transducer includes a body with one open side and piezoelectric elements, the body is filled with air, and each piezoelectric element is connected with an electric wire to apply voltage. The piezoelectric element uses a material exhibiting a piezoelectric effect such as quartz and tourmaline, and the transducer may generate and output ultrasound using the piezoelectric effect of the piezoelectric element. The structure of the transducer is provided for illustration purposes only, and the transducer is not limited to a particular structure or effect. The piezoelectric element of the transducer may output a proper intensity of ultrasound by adjusting the output according to a target part to be treated and the purpose, and the outputted ultrasound has an overlap, forming an ultrasound beam.

As shown in FIG. 3B, the ultrasound output unit 100 irradiates high intensity focused ultrasound onto a tissue T in which a lesion to be removed is present. A focal point F is a spot onto which the ultrasound beam outputted from the transducer is focused, and oscillating energy by ultrasound converges into one to produce a strong nonlinear shockwave. A vapor bubble having the size of a few hundred μm to a few mm is formed at the focal point F by the shock wave heating and the bubble oscillates and collapses, producing mechanical stresses, and the tissue is mechanically fractionated by the formation and dynamics of the vapor bubble (mechanical ablation).

In another embodiment, the focused ultrasound outputted by the ultrasound output unit 100 does not have the pressure that is high enough to produce a shockwave, but may have a linear or nonlinear waveform having a high frequency to quickly increase the temperature. Also in this case, like the way the shockwave is produced, a vapor bubble is formed in the tissue by the thermal effect.

Figure 2A:
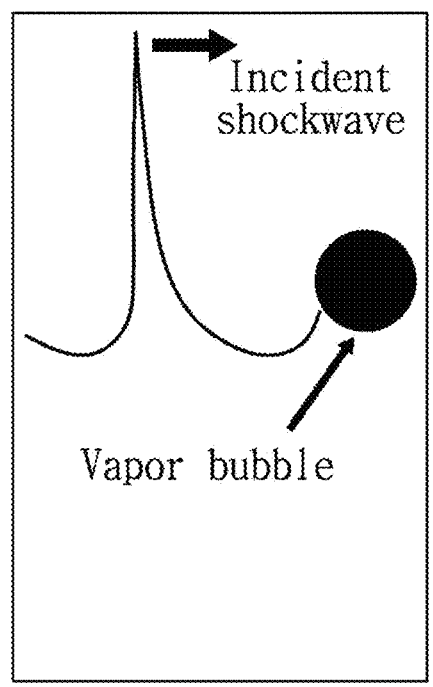
FIGS. 2A to 2C are diagrams illustrating the principle of the shock scattering effect and bubble cloud formation in the process of tissue ablation using focused ultrasound according to the related art.
Figure 2B:
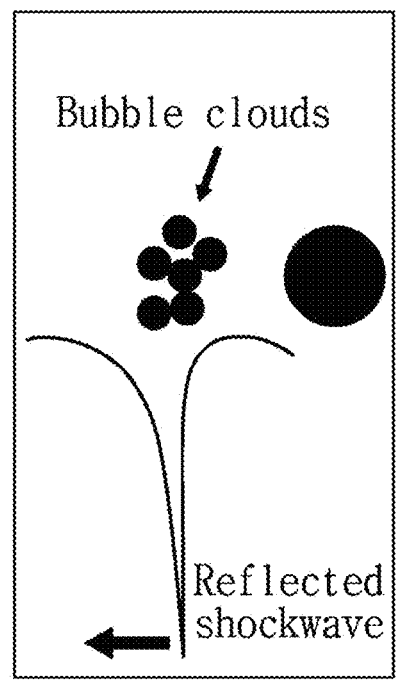
Figure 2C:
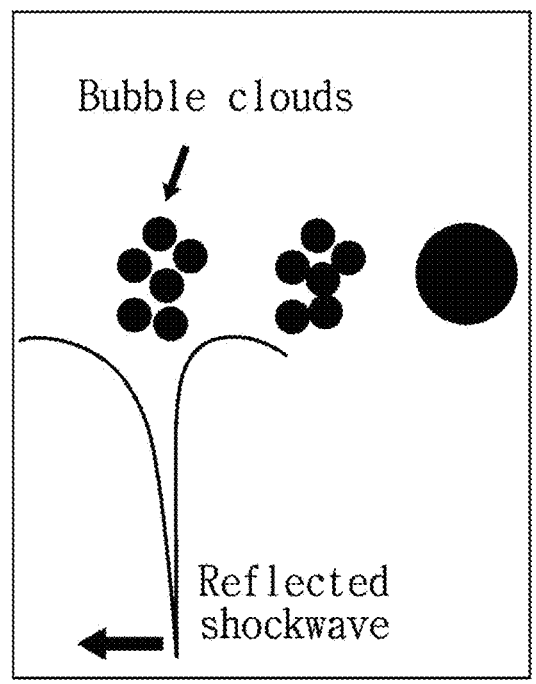

As described above, boiling histotripsy may have the shock scattering effect by interaction between the vapor bubble and the incoming incident shockwave. Numerous bubble clouds are formed between the HIFU transducer and the primary boiling bubble by the shock scattering effect, and these bubble clouds produce a mechanical stress at areas other than the focal point position, causing damage to an unwanted tissue part. The present disclosure relates to precise control of vapor bubble dynamics while preventing the shock scattering effect. As described with reference to FIGS. 2A to 2C, the shock scattering effect results from the interaction between the incoming incident ultrasound and a vapor bubble. Accordingly, it is possible to prevent the generation of bubble clouds due to the shock scattering effect by controlling the acoustic pressure, the frequency, the waveform and/or the irradiation time of focused ultrasound to reducing the intensity of focused ultrasound.

The detection unit 200 is a component for determining the time to reduce the pressure and/or intensity of focused ultrasound, and when a vapor bubble is formed in the tissue (first condition), or the temperature of the tissue reaches the threshold (second condition) during the output of focused ultrasound to the tissue, the detection unit 200 is configured to detect it and transmit it to the control unit 300. Immediately after the first condition or the second condition is accomplished, it is possible to prevent the generation of bubble clouds due to the shock scattering effect by controlling the pressure and/or intensity of focused ultrasound to a low level.

In an embodiment, the detection unit 200 may have a signal sensor to sense a change in acoustic signal or electrical signal caused by vapor bubble formation to detect if the first condition is accomplished. In another embodiment, the detection unit 200 may have a temperature sensor to sense a change in temperature of the tissue to detect if the second condition is accomplished.

Describing the first condition, when a primary vapor bubble is formed by the shock wave heating, secondary bubble clouds are formed by the interaction between a shockwave reflected by the bubble and an incident shockwave, causing damage to the tissue. Accordingly, it is possible to prevent the shock scattering effect by reducing the pressure and/or intensity of focused ultrasound to a level at which a shockwave is not produced at the focal point after the first condition is accomplished (for example, after the primary vapor bubble is formed). When the vapor bubble is formed in the tissue by the shockwave, then an acoustic signal or an electrical signal is generated, and according to an embodiment, the detection unit 200 has a signal sensor to sense the signal, and when the signal of a specific waveform is sensed, vapor bubble formation is determined.

Describing the second condition, the shockwave produced at the focal point increases the temperature of water in the tissue (shock wave heating) to generate a vapor bubble (boiling effect), and after the second condition is accomplished (for example, after the temperature in the tissue reaches 100° C.), when the pressure and/or intensity of focused ultrasound are reduced down to a level at which a shockwave is not produced, likewise, it is possible to prevent the shock scattering effect. Of course, the threshold of the temperature for accomplishing the second condition may be differently set depending on various factors such as the purpose or the area of the target part. In an embodiment, the detection unit 200 may have a temperature sensor to sense a temperature change, in order to determine that the temperature in the tissue reaches the threshold.

In this specification, the description is made using the first condition and the second condition as an example, but this is provided by way of illustration, and a different condition (a third condition or a fourth condition) may be set, various types of sensors suitable to detect if the corresponding condition is accomplished may be used.

The control unit 300 is configured to receive the output as to whether the first condition (a vapor bubble is formed in the tissue) or the second condition (the temperature of the tissue reaches the threshold) is accomplished from the detection unit 200, and when the condition is accomplished, controls the ultrasound output unit 100 to adjust the pressure and intensity of output focused ultrasound. In detail, the control unit 300 controls the intensity of focused ultrasound below a setting value by adjusting the parameters of ultrasound outputted from the ultrasonic transducer such as acoustic pressure, waveform, frequency and/or irradiation time.

Here, the setting value refers to the maximum intensity value at which focused ultrasound does not produce the shock scattering effect within the tissue. For example, when the first condition or the second condition is accomplished during the output of high intensity focused ultrasound (HIFU) having the the peak positive acoustic pressure of 40 MPa or above and the peak negative pressure of −10 MPa or below at the focal point, the ultrasound output unit 100 may adjust the acoustic pressure of focused ultrasound to the peak positive pressure of 40 MPa or below and the peak negative pressure of −10 MPa or above to prevent the shock scattering effect and consequential bubble cloud formation.

In another embodiment, when the condition is accomplished during the output of focused ultrasound having the shockwave pressure of 50 MPa or above at the focal point, the shockwave pressure may be reduced down to 50 MPa or below. Alternatively, when the first condition or the second condition is accomplished, the control unit may control the ultrasound output unit not to output focused ultrasound any longer, so that part or all the tissue may be removed only using a mechanical stress produced when a vapor bubble is formed.

The setting value may be differently set depending on the type of tissue and the characteristics of focused ultrasound. For example, as the stiffness of the tissue is higher, the intensity of ultrasound for producing the shock scattering effect may be higher, and in this case, the setting value may be set to a higher level.

In still another embodiment, the control unit 300 may be configured to control the intensity of focused ultrasound below the setting value, when the period of time has passed from the start time of the output of focused ultrasound to the tissue, based on information about the time required to accomplish the first condition or the second condition without using the detection unit 200.

Figure 6A:
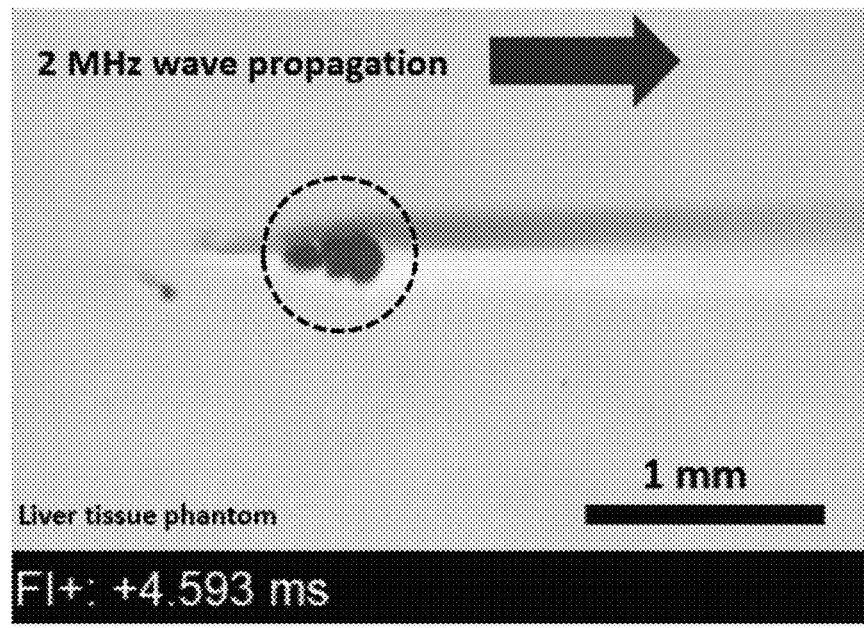
FIGS. 6A to 6C show experimental results of applying tissue ablation using intensity modulated focused ultrasound according to an embodiment to a tissue-mimicking gel phantom.
Figure 6B:
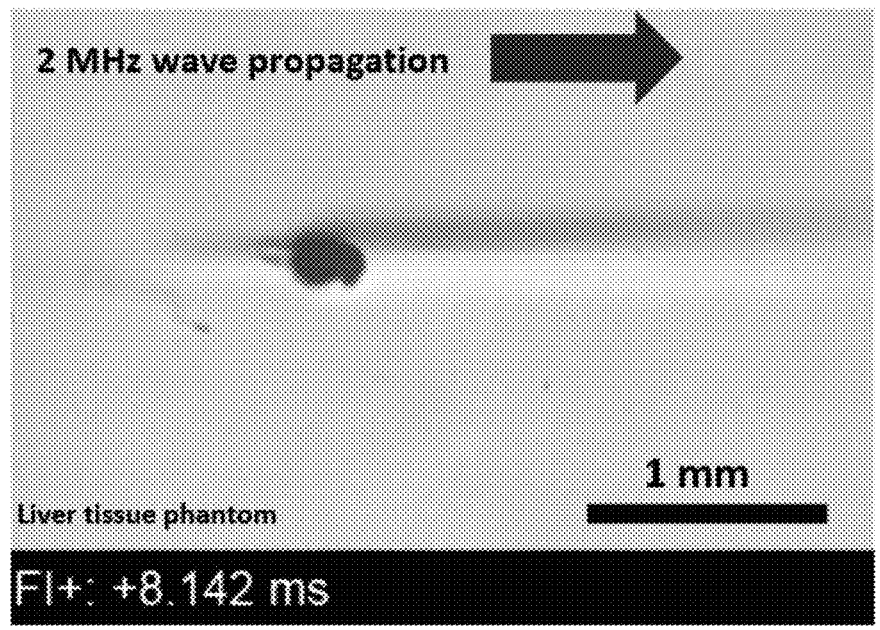
Figure 6C:
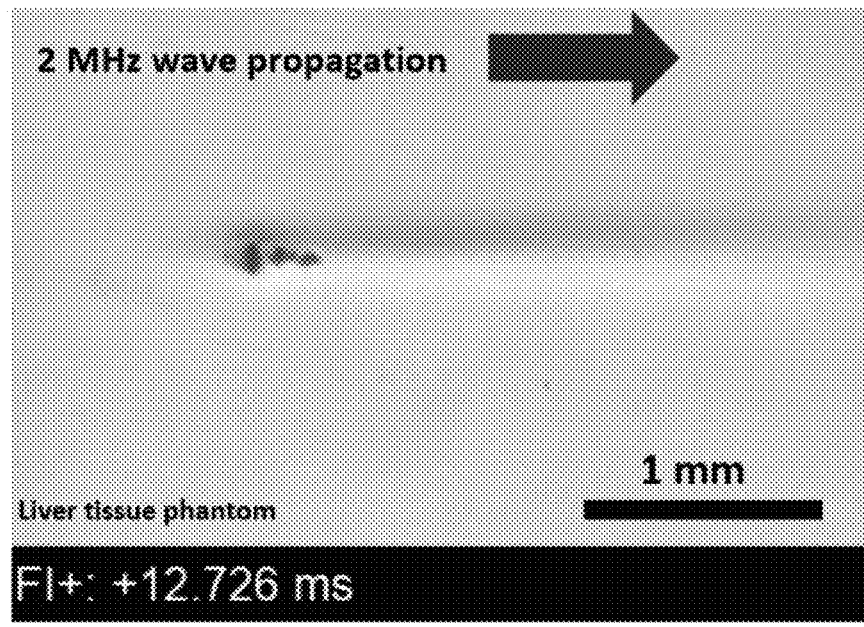

According to this embodiment, vapor bubble formation or a temperature change is not directly sensed using a sensor, and instead, the time required to form the vapor bubble or the time required for the temperature to reach the threshold in the set condition may be determined through simulation, and after the corresponding time passed away, the pressure and intensity of focused ultrasound may be automatically controlled. For example, through simulation, when high intensity ultrasound having the frequency of 2 MHz and the acoustic pressure characteristics of the peak positive pressure of 92 MPa and the peak negative pressure of −14 MPa at the focal point is outputted to a tissue-mimicking gel phantom having similar physical properties to the tissue, it can be seen that the time for the temperature at the focal point part to reach 100° C. is about 3.84 ms. In case that the information is pre-inputted into the apparatus 10 for tissue ablation, high intensity ultrasound having the acoustic pressure characteristics of the peak positive pressure of 92 MPa and the peak negative pressure of −14 MPa may be outputted between 0 to 3.84 ms, and the acoustic pressure of the peak positive pressure and the peak negative pressure of ultrasound may be respectively reduced to 30 MPa and −9.4 MPa after 3.84 ms. Its experimental result is shown in FIGS. 6A to 6C, and it can be seen from the result that only the focal point part of the tissue is precisely removed.

The time taken to accomplish the first condition or the second condition (in the above example, 3.84 ms) may be determined based on biomechanics information, thermodynamics information and bubble dynamics information. The rising temperature trend of the tissue by ultrasound and vapor bubble dynamics may be predicted using Bioheat transfer equation and Gilmore bubble equation. In other words, when it is combined with ultrasound irradiation condition (acoustic pressure, waveform, frequency and irradiation time of ultrasound), it is possible to predict information, for example, the time required for the tissue to reach a specific temperature, the size of a vapor bubble that will be formed, and vapor bubble dynamics in a given acoustic field. It is possible to automatically control the intensity of ultrasound without a senor by pre-inputting time information required to accomplish the condition.

According to the above-described embodiment, it is possible to control vapor bubble dynamics by artificially forming a vapor bubble at the focal point of ultrasound using a strong nonlinear shockwave produced by the ultrasonic transducer, and reducing the intensity of focused ultrasound below the setting value by instantaneously changing the acoustic pressure and waveform of ultrasound when a specific condition is accomplished. After control, the acoustic pressure of ultrasound is lower than the absolute pressure value at which the shock scattering effect takes place, and thus the shock scattering effect-induced acoustic cavitation is not created at areas other than the area in which a vapor bubble is formed at the focal point of ultrasound. Accordingly, it is possible to precisely remove the tissue (a tumor tissue, etc.) only using a mechanical stress produced by predictable and controllable vapor bubble dynamics. That is, the present disclosure relates to focused ultrasound soft tissue ablation that can be applied to lesions of various sizes and locations through precise spatiotemporal control of acoustic cavitation.

Figure 4A:
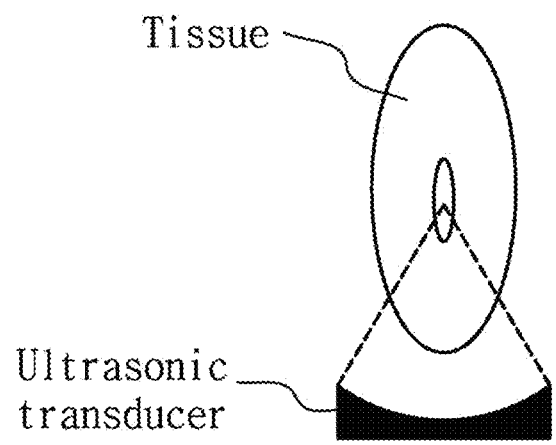
FIGS. 4A to 4C show a tissue ablation process using focused ultrasound according to an embodiment.
Figure 4B:
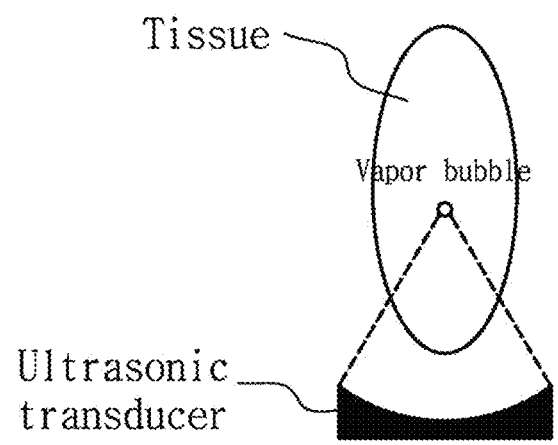
Figure 4C:
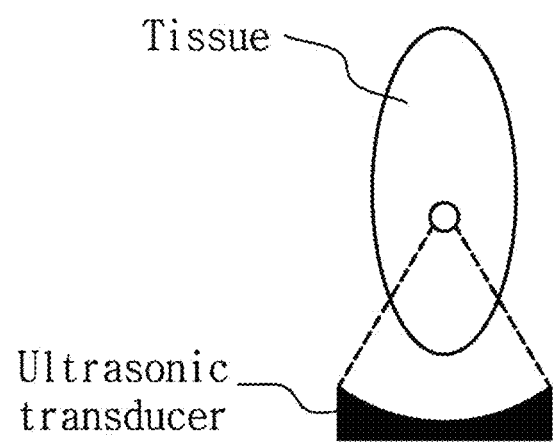

FIGS. 4A to 4C show a mechanical tissue ablation process using focused ultrasound according to an embodiment. According to an embodiment, focused ultrasound of the center frequency: 0.1-30 MHz, the pulse length: 0.1-100 ms, the pulse repetition frequency: 0.1-10 Hz, and the number of pulses: one or more, may be used. The focal point pressure value used from the beginning to vapor bubble formation is $P_+>40$ MPa, $P_-<-10$ MPa, and after bubble formation, may be controlled to $P_+<40$ MPa, $P_->-10$ MPa (that is, the absolute value of acoustic pressure decreases and the intensity decreases).

Referring to FIG. 4A, when high intensity focused ultrasound outputted by the ultrasonic transducer produces a strong shockwave at the focal point position, the temperature of the tissue rises due to the shockwave heating (the center frequency of ultrasound: 0.1-5 MHz). Alternatively, as described above, focused ultrasound having the center frequency that is high enough to rapidly increase the temperature, but the pressure that is not high enough to produce a shockwave may be used (the center frequency of ultrasound: 5-30 MHz, in this case, the focal length may be shorter). Referring to FIG. 4B, when the temperature of water in the tissue increases, a vapor bubble is formed at the focal point position. Referring to FIG. 4C, when vapor bubble formation or the temperature reaching the threshold is sensed, the control unit controls the intensity of focused ultrasound below the setting value. As a result, there is no shock scattering effect and consequential bubble cloud formation, and the cavitation-induced ablation area is limited to the focal point position.

Figure 5A:
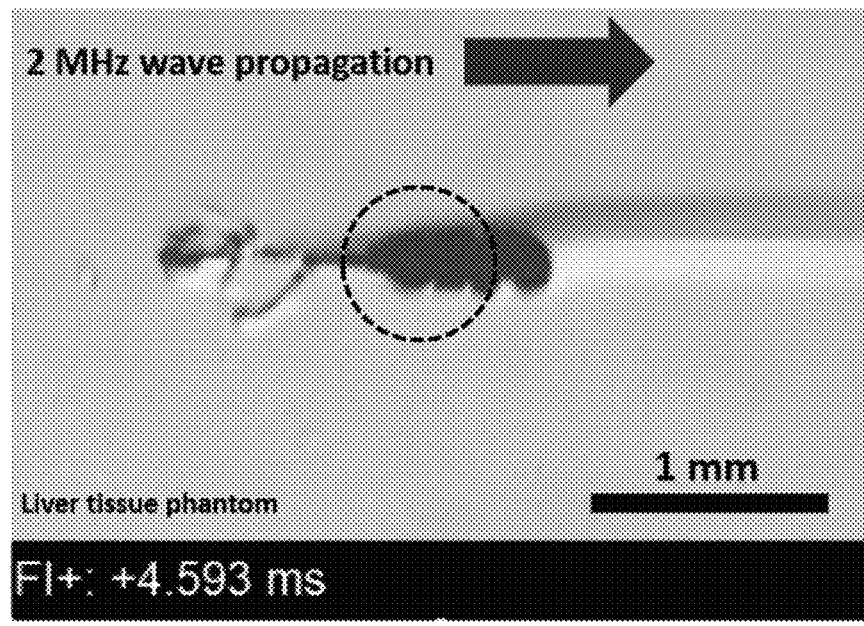
FIGS. 5A to 5C show experimental results of applying tissue ablation using focused ultrasound according to the related art to a tissue-mimicking gel phantom.
Figure 5B:
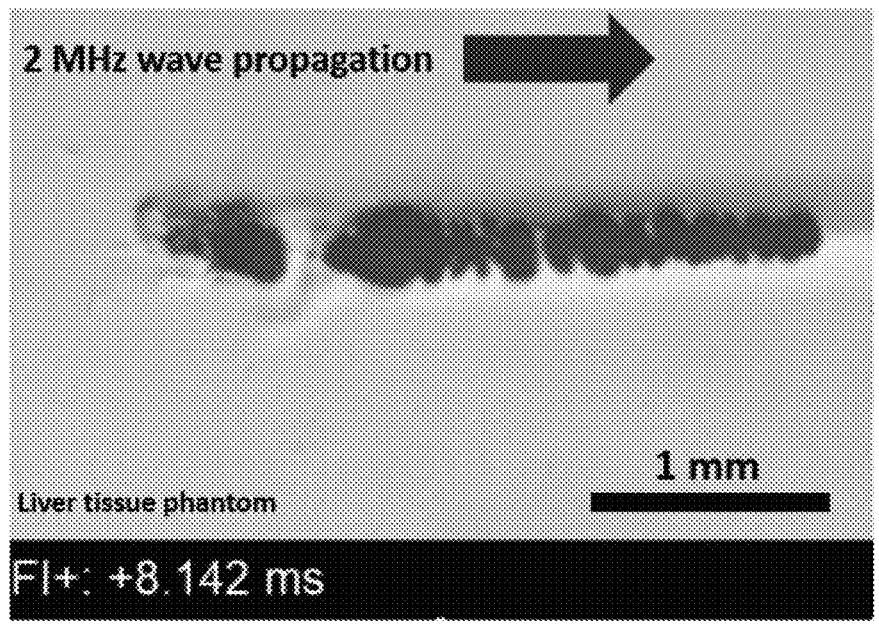
Figure 5C:
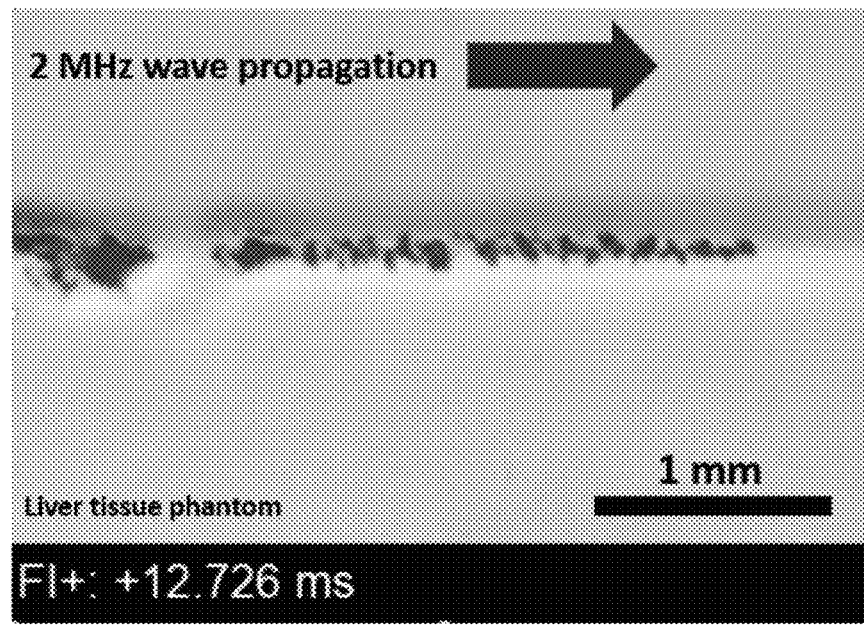

FIGS. 5A to 5C show experimental results of applying tissue ablation according to the related art to a tissue-mimicking gel phantom, and FIGS. 6A to 6C show experimental results of applying tissue ablation according to an embodiment to a tissue-mimicking gel phantom.

In the experimental example of FIGS. 5A to 5C, an image is captured using a high-speed camera during irradiation of high intensity focused ultrasound with the frequency of 2 MHz having the irradiation time of 10 ms to the tissue-mimicking gel with the acoustic pressure being fixed to $P_+=92$ MPa, $P_-=-14$ MPa (the photographing time is 0-13 ms). According to the simulation, the time required for the temperature of the gel phantom to reach 100° C. is 3.84 ms. Referring to FIG. 5A, a vapor bubble is formed at the focal point position (indicated by a dashed circle), but as shown in FIG. 5B, bubble clouds are formed at areas other than the focal point position due to the shock scattering effect. As a result, as shown in FIG. 5C, a mechanical stress is applied to areas other than the focal point position due to the bubble clouds.

FIGS. 6A to 6C show a result of applying tissue ablation using pressure modulated ultrasound according to an embodiment of the present disclosure. In the experimental example, high intensity focused ultrasound having the frequency of 2 MHz and $P_+=92$ MPa, $P_-=-14$ MPa is irradiated onto a tissue-mimicking gel phantom in the range of 0-4 ms, and after a bubble is formed, the acoustic pressure of ultrasound is adjusted to $P_+=30$ MPa, $P_-=-9.4$ MPa in the range of 4-10 ms. Referring to FIG. 6A, a vapor bubble is formed at the focal point position (indicated by a dashed circle) but the shock scattering effect is not produced through ultrasound intensity control, and accordingly, as shown in FIG. 6B, bubble cloud is not formed at areas other than focal point position. As a result, as shown in FIG. 6C, a mechanical stress is only applied to the focal point position and other areas are not removed.

Figure 7A:
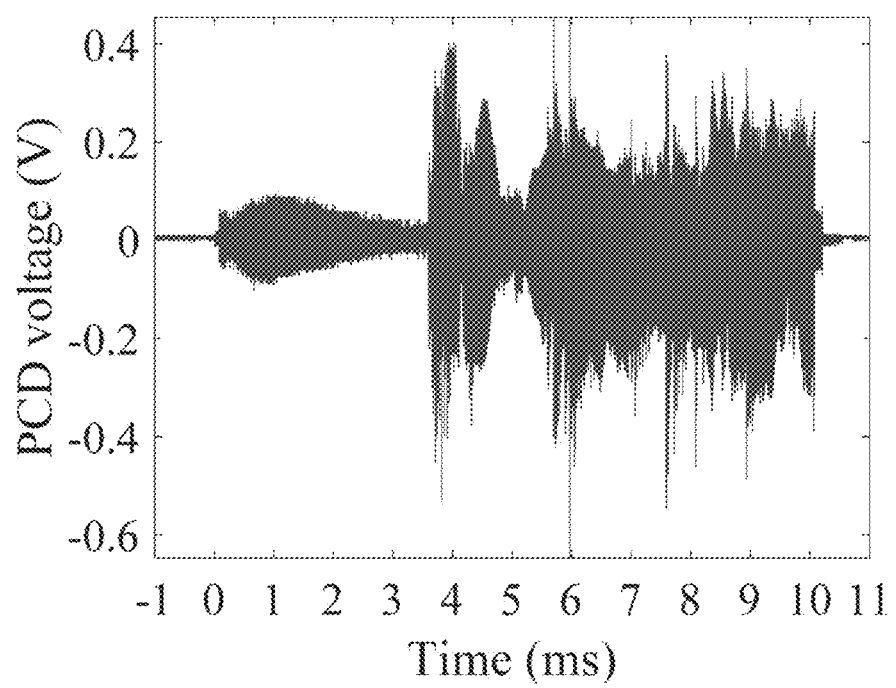
FIGS. 7A and 7B show the results of monitoring PCD (Passive Cavitation Detection) voltage signals after applying tissue ablation using intensity modulated focused ultrasound according to an embodiment and tissue ablation according to the related art to tissue-mimicking gel phantoms.

FIG. 7A shows a result of monitoring a PCD voltage signal after applying tissue ablation (during boiling histotripsy exposure) according to the related art to a tissue-mimicking gel phantom. Referring to FIG. 7A, it can be seen that PCD voltage increases rapidly at the point of 4 ms due to vapor bubble formation, and afterwards, an unstable voltage change is sensed due to bubble clouds.

Figure 7B:
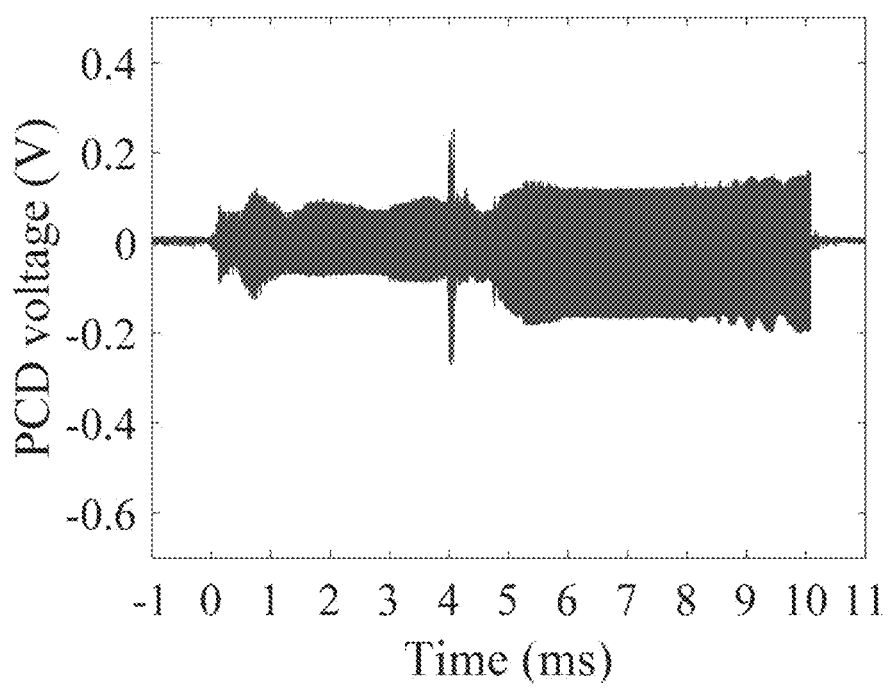

FIG. 7B shows a result of monitoring a PCD voltage signal after applying tissue ablation using pressure modulated focused ultrasound according to an embodiment to a tissue-mimicking gel phantom. Referring to FIG. 7B, it can be seen that PCD voltage increases rapidly at the point of 4 ms due to vapor bubble formation but is stabilized through ultrasound intensity control.

Figure 8A:
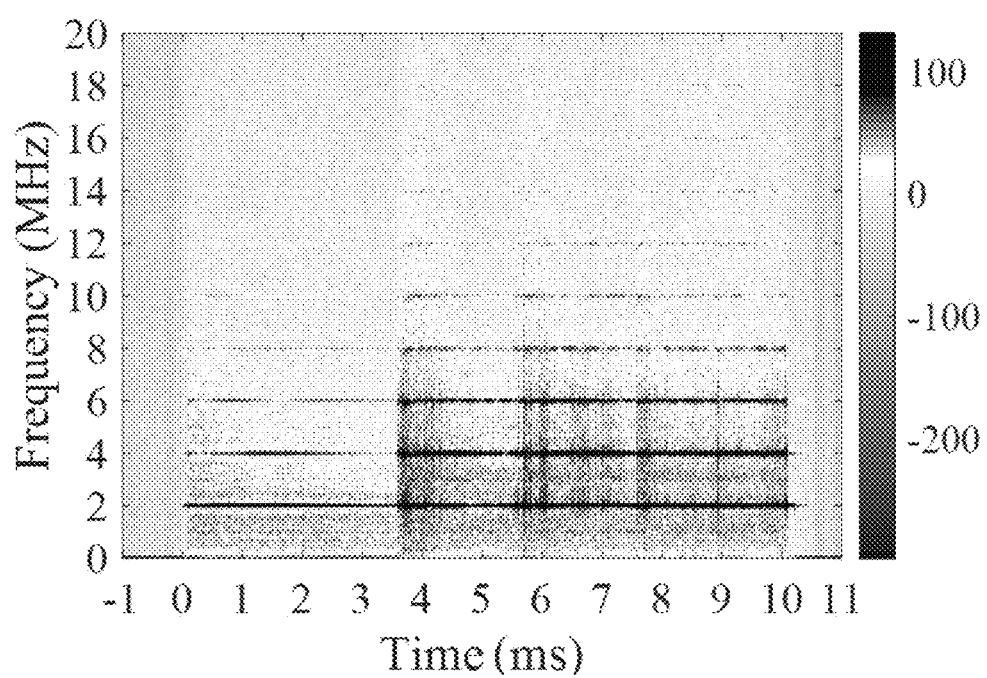
FIGS. 8A and 8B show the results of monitoring frequency changes after applying tissue ablation using intensity modulated focused ultrasound according to an embodiment and tissue ablation according to the related art to tissue-mimicking gel phantoms.
Figure 8B:
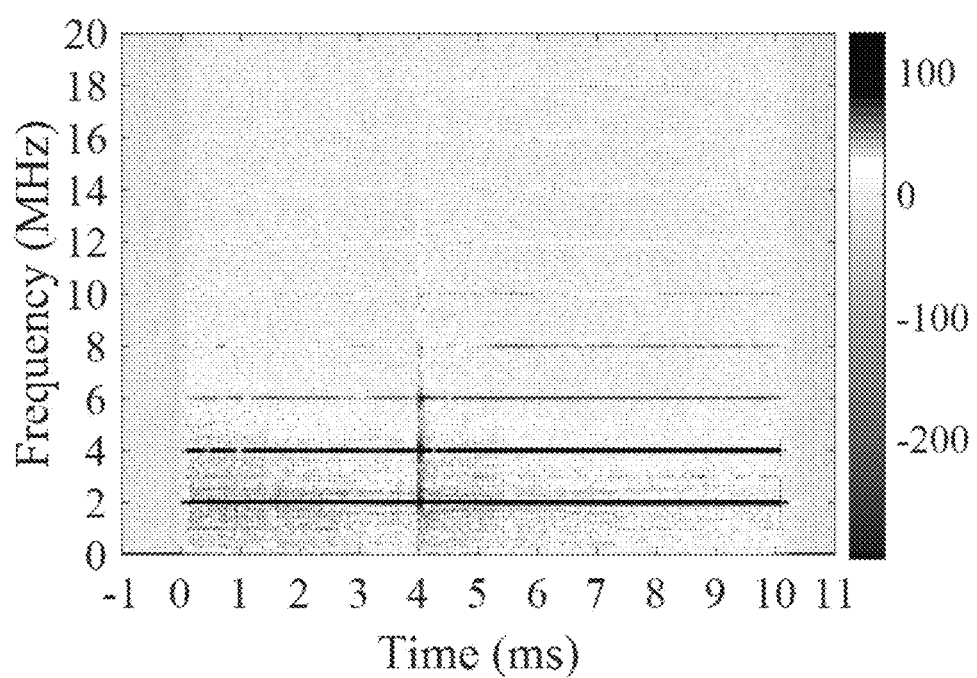

FIG. 8A shows a result of monitoring a frequency change after applying tissue ablation (during boiling histotripsy exposure) according to the related art to a tissue-mimicking gel phantom, and it can be seen that significant appearance of broadband emissions (an indication of inertial cavitation clouds) is sensed after the formation of a boiling bubble at 3.84 ms. In contrast, FIG. 8B shows a result of monitoring a frequency change after applying tissue ablation using pressure modulated focused ultrasound according to an embodiment to a tissue-mimicking gel phantom, and it can be seen that no significant appearance of broadband emissions is detected after 4 ms. From this, it can be seen that there is no shock scattering effect and bubble cloud formation by use of pressure modulated focused ultrasound according to an embodiment.

As such, using the apparatus for tissue ablation according to an embodiment, it is possible to control vapor bubble dynamics through pressure and/or intensity modulated focused ultrasound, and precisely remove the tissue only using a mechanical stress produced by the predictable and controllable vapor bubble dynamics.

As an embodiment generates a vapor bubble by maximizing the thermal effect, both thermal ablation and mechanical ablation are possible in the ultra small ultrasonic transducer applications (for example, a transducer as small as an endoscopic probe). The acoustic pressure is proportional to the surface area size of the ultrasonic transducer, while the frequency of ultrasound is inversely proportional to the thickness of the transducer, and the effect of the present disclosure can be obtained from high intensity ultrasound having high frequency and thus it is possible to use in ultra small transducer applications.

Figure 9:
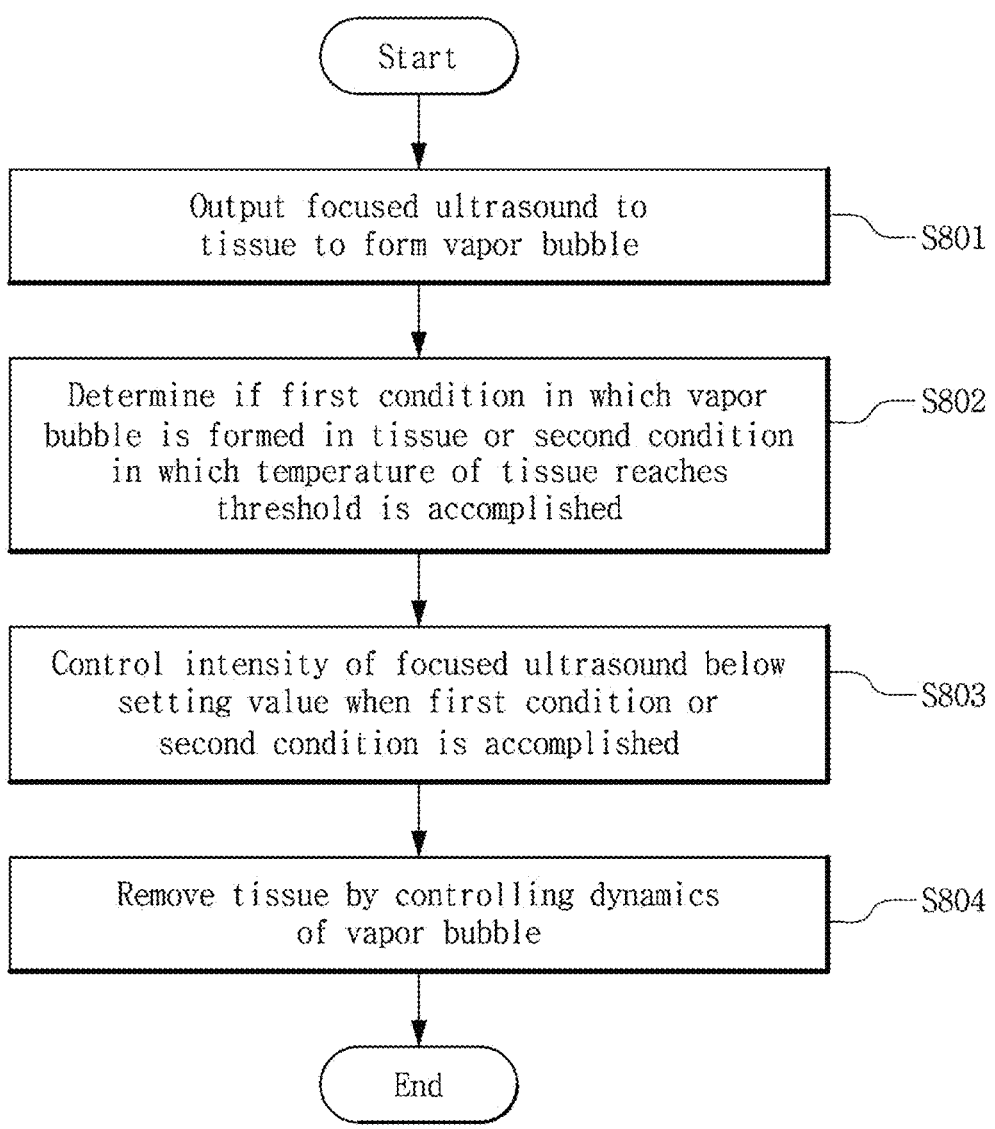
FIG. 9 is a flowchart showing a method for tissue ablation using intensity modulated focused ultrasound according to an embodiment.

FIG. 9 is a flowchart showing a method for tissue ablation using pressure and/or intensity modulated focused ultrasound according to an embodiment.

According to an embodiment, first, the step of outputting focused ultrasound to a tissue is performed (S801). To produce focused ultrasound, an ultrasonic transducer may be used, and the ultrasonic transducer outputs high intensity focused ultrasound to the tissue in which a lesion to be removed is present. The focused ultrasound may produce a strong nonlinear shockwave or rapidly increases the temperature at the focal point position.

Subsequently, the step of determining if a first condition in which a vapor bubble is formed in the tissue or a second condition in which the temperature of the tissue reaches the threshold is accomplished (S802). As described above, to detect if each condition is accomplished, a signal sensor may be used to sense a change in acoustic signal or electrical signal caused by vapor bubble formation, or a temperature sensor may be used to sense a change in temperature of the tissue. The step of sensing a change in acoustic signal or electrical signal caused by vapor bubble formation; or a change in temperature of the tissue using these sensors may be further performed.

Subsequently, when the first condition or the second condition is accomplished, the step of controlling the intensity of focused ultrasound below the setting value is performed (S803). According to an embodiment, it is possible to control the intensity of focused ultrasound below the setting value by adjusting the parameters of ultrasound outputted from the ultrasonic transducer such as acoustic pressure, waveform, frequency and irradiation time. The setting value refers to the maximum intensity value at which ultrasound does not produce the shock scattering effect within the tissue, and when ultrasound is controlled below the setting value, bubble cloud formation at areas other than the focal point position is suppressed. For example, in S801, focused ultrasound may be set to have the acoustic pressure of the peak positive pressure of 40 MPa or above and the peak negative pressure of −10 MPa or below at the focal point, and after S803, focused ultrasound may be set to have the acoustic pressure of the peak positive pressure of 40 MPa or below, and the peak negative pressure of −10 MPa or above at the focal point.

Finally, the step of removing part of the tissue using dynamics of the vapor bubble formed in the tissue is performed (S804). The vapor bubble oscillates and collapses, producing a mechanical stress, thereby mechanically removing the lesion at the focal point position.

FIG. 10 is a flowchart showing a method for tissue ablation using intensity modulated focused ultrasound according to another embodiment.

According to an embodiment, the step of receiving information about the time required to form a vapor bubble in the tissue (first condition) or the time for the temperature of the tissue to reach the threshold (second condition) is performed (S901).

According to this embodiment, the time required to accomplish each condition may be determined through simulation. For example, when high intensity ultrasound having the frequency of 2 MHz and the shockwave pressure characteristics of 106 MPa is outputted to the tissue-mimicking gel phantom, a simulation result that the time required for the temperature at the focal point part to reach 100° C. is about 3.84 ms is obtained, the information may be pre-inputted.

Subsequently, the step of outputting focused ultrasound to the tissue is performed (S902). S902 is performed in the similar way to S802, and a redundant description is omitted herein.

Subsequently, when the time has passed from the output of the focused ultrasound, the step of controlling the intensity of focused ultrasound below the setting value is performed (S903). That is, it is possible to automatically control the intensity of ultrasound without a special sensor by pre-inputting the time required to accomplish the first condition or the second condition (in the above example, 3.84 ms). S903 may be performed by a control device, a control system, a single or multiple processor units connected to the transducer.

Finally, the step of removing part of the tissue using dynamics of the vapor bubble formed in the tissue is performed (S904). In the same way to S804 of FIG. 9, the vapor bubble oscillates and collapses, producing a mechanical stress, thereby mechanically removing the lesion at the focal point position.

The method for tissue ablation using intensity modulated focused ultrasound according to an embodiment may be implemented, in whole or in part, as an application or in the form of program instructions that may be executed through various computer components and may be recorded in a computer-readable recording medium. The computer-readable recording medium may include program instructions, data files and data structures, alone or in combination.

Examples of the computer-readable recording medium include hardware devices specially designed to store and execute program instructions, for example, magnetic media such as hard disk, floppy disk and magnetic tape, optical media such as CD-ROM and DVD, magneto-optical media such as floptical disk, and ROM, RAM and flash memory.

According to the apparatus and method for tissue ablation using pressure and/or intensity modulated or pulse modulated focused ultrasound as described above, it is possible to precisely control vapor bubble dynamics without inducing the shock scattering effect by instantaneously controlling the pressure and/or intensity of focused ultrasound when a vapor bubble is formed in the tissue or the temperature reaches the threshold during the output of focused ultrasound to the tissue. Accordingly, it is possible to prevent damage to an unwanted part other than the lesion, and improve the precision of tissue ablation. Therefore, it is possible to selectively remove only a specific cell through high precision control of vapor bubble.

While the present disclosure has been hereinabove described with reference to the embodiments, it will be understood by those having ordinary skill in the corresponding technical field that various modifications and changes may be made to the present disclosure without departing from the spirit and scope of the present disclosure defined by the appended claims.

What is claimed is:

1. An apparatus for tissue ablation using pressure modulated focused ultrasound, the apparatus comprising:
   an ultrasound transducer configured to output focused ultrasound to a tissue; and
   a controller configured to:
      control an intensity of the focused ultrasound by adjusting an acoustic pressure of the focused ultrasound;
      control the acoustic pressure of the focused ultrasound to adjust the intensity of the focused ultrasound to be below a predetermined setting value of the intensity of the focused ultrasound when a first condition occurs in which a vapor bubble is formed in the tissue during the output of the focused ultrasound to the tissue;
      control the acoustic pressure of the focused ultrasound below the predetermined setting value of the intensity of the focused ultrasound when a second condition occurs in which a temperature of the tissue reaches a threshold during the output of the focused ultrasound to the tissue;
      control the acoustic pressure of the focused ultrasound below the predetermined setting value of the intensity of the focused ultrasound when a predetermined time required to reach the first condition has passed from a start of the output of the focused ultrasound to the tissue, based on information about the predetermined time required to reach the first condition; and
      control the acoustic pressure of the focused ultrasound below the predetermined setting value of the intensity of the focused ultrasound when a predetermined time required to reach the second condition has passed from the start of the output of the focused ultrasound to the tissue, based on information about the predetermined time required to reach the second condition,
   wherein the focused ultrasound having an intensity below the predetermined setting value does not produce a shock scattering effect in the tissue.

2. The apparatus according to claim 1, wherein the predetermined setting value of the intensity of the focused ultrasound is set according to a type of the tissue and characteristics of the focused ultrasound.

3. The apparatus according to claim 1, wherein the controller is further configured to control the intensity of the focused ultrasound by adjusting a waveform, a frequency, or an irradiation time of the focused ultrasound outputted from the ultrasound transducer.

4. The apparatus according to claim 3, wherein the ultrasound transducer is configured to output high intensity focused ultrasound having a shockwave pressure of 50 MPa or above or a peak positive acoustic pressure of 40 Mpa or above and a peak negative pressure of −10 Mpa or below, and
   wherein when the first condition occurs or when the second condition occurs, the controller controls the shockwave pressure of the focused ultrasound below 50 Mpa or to below the peak positive acoustic pressure of 40 Mpa and above the peak negative pressure of −10 Mpa.

5. The apparatus according to claim 1, further comprising:
   a first detector configured to detect when the first condition occurs,
   wherein the first detector includes a signal sensing device to sense a change in an acoustic signal or an electrical signal caused by vapor bubble formation and dynamics.

6. The apparatus according to claim 1, further comprising:
   a second detector configured to detect when the second condition occurs,
   wherein the second detector includes a temperature sensor to sense a change in the temperature of the tissue.

7. The apparatus according to claim 1, wherein the predetermined time required to reach the first condition and the predetermined time required to reach the second condition are determined, through simulation, based on characteristics of the focused ultrasound, using biomechanics information, thermodynamics information and bubble dynamics information.

8. The apparatus according to claim 1, when the first condition occurs, when the second condition occurs, when the predetermined time required to reach the first condition has passed, or when the predetermined time required to reach the second condition has passed, the controller controls the ultrasound transducer not to output the focused ultrasound, so that a part of the tissue is removed only using a mechanical stress produced when the vapor bubble is formed.

9. A method for controlling focused ultrasound for precise tissue ablation, the method comprising:
  outputting focused ultrasound to a tissue;
  determining when a first condition occurs in which a vapor bubble is formed in the tissue;
  determining when a second condition occurs in which a temperature of the tissue reaches a threshold;
  controlling an acoustic pressure of the focused ultrasound to adjust an intensity of the focused ultrasound to be below a predetermined setting value of the intensity of the focused ultrasound when the first condition occurs;
  controlling the acoustic pressure of the focused ultrasound below the predetermined setting value of the intensity of the focused ultrasound when the second condition occurs;
  receiving information about a predetermined time required to reach the first condition;
  receiving information about a predetermined time required to reach the second condition;
  controlling the acoustic pressure of the focused ultrasound below the predetermined setting value of the intensity of the focused ultrasound when the predetermined time required to reach the first condition has passed from a start of the outputting the focused ultrasound to the tissue;
  controlling the acoustic pressure of the focused ultrasound below the predetermined setting value of the intensity of the focused ultrasound when the predetermined time required to reach the second condition has passed from the start of the outputting the focused ultrasound to the tissue; and
  removing a part of the tissue using dynamics of the vapor bubble formed in the tissue,
  wherein the focused ultrasound having an intensity below the predetermined setting value does not produce a shock scattering effect in the tissue, and
  wherein the intensity of the focused ultrasound is controlled by adjusting the acoustic pressure.

10. The method according to claim 9, wherein the predetermined setting value of the intensity of the focused ultrasound is differently set depending on a type of the tissue and characteristics of the focused ultrasound.

11. The method according to claim 9, wherein the intensity of the focused ultrasound is further controlled by adjusting a waveform, an irradiation time or a frequency of the focused ultrasound.

12. The method according to claim 11, wherein in the outputting the focused ultrasound to the tissue, the focused ultrasound has a shockwave pressure of 50 MPa or above or a peak positive acoustic pressure of 40 MPa or above and a peak negative pressure of −10 MPa or below, and
  wherein the focused ultrasound after controlling the intensity of the focused ultrasound below the predetermined setting value has the shockwave pressure of less than 50 MPa or below the peak positive acoustic pressure of 40 MPa and above the peak negative pressure of −10 MPa.

13. The method according to claim 9, wherein the determining when the first condition occurs comprises sensing a change in an acoustic signal or an electrical signal caused by vapor bubble formation and dynamics, and
  wherein the determining when the second condition occurs comprises sensing a change in the temperature of the tissue.

14. The method according to claim 9, wherein the predetermined time required to reach the first condition and the predetermined time required to reach the second condition are determined, through simulation, based on characteristics of the focused ultrasound, using biomechanics information, thermodynamics information and bubble dynamics information.

15. The method according to claim 9, wherein controlling the acoustic pressure of the focused ultrasound below the predetermined setting value comprises:
  stopping the outputting the focused ultrasound when the first condition occurs, when the second condition occurs, when the predetermined time required to reach the first condition has passed, or when the predetermined time required to reach the second condition has passed; and
  removing the part of the tissue is performed only using a mechanical stress produced when the vapor bubble is formed.

16. A non-transitory computer readable storage medium storing a computer program for performing the method according to claim 9.

* * * * *